US010139260B2

(12) United States Patent
van der Schoot et al.

(10) Patent No.: US 10,139,260 B2
(45) Date of Patent: Nov. 27, 2018

(54) METHOD FOR CONTROLLING PIPETTING OPERATIONS

(71) Applicant: SEYONIC S.A., Neuchâtel (CH)

(72) Inventors: Bart van der Schoot, Neuchâtel (CH); Yari Luchessa, Lussery-Villars (CH); Marc Boillat, Auvernier (CH)

(73) Assignee: Seyonic S.A., Neuchâtel (CH)

( * ) Notice: Subject to any disclaimer, the term of this patent is extended or adjusted under 35 U.S.C. 154(b) by 87 days.

(21) Appl. No.: 14/392,332

(22) PCT Filed: Apr. 1, 2014

(86) PCT No.: PCT/EP2014/056551
§ 371 (c)(1),
(2) Date: Dec. 24, 2015

(87) PCT Pub. No.: WO2014/206588
PCT Pub. Date: Dec. 31, 2014

(65) Prior Publication Data
US 2016/0273951 A1    Sep. 22, 2016

(30) Foreign Application Priority Data
Jun. 24, 2013    (EP) .................................... 13173422

(51) Int. Cl.
*G01F 11/00* (2006.01)
*B01L 3/02* (2006.01)
(Continued)

(52) U.S. Cl.
CPC ............ *G01F 11/029* (2013.01); *B01L 3/021* (2013.01); *G01F 25/0092* (2013.01); *G01N 1/14* (2013.01);
(Continued)

(58) Field of Classification Search
CPC .. G01F 11/029; G01F 25/0092; G01F 1/8436; G01F 25/0007; G01F 15/024;
(Continued)

(56) References Cited

U.S. PATENT DOCUMENTS 4,896,270 A  *  1/1990  Kalmakis .............. B01L 3/0227
                                                        422/562
6,280,389 B1 *  8/2001  Ding ...................... A61N 1/365
                                                        600/485
(Continued)

FOREIGN PATENT DOCUMENTS

EP      2 031 403 A1    3/2009
WO      01/88549 A1    11/2001

OTHER PUBLICATIONS

Chen, L., et al., "Intelligent Control of Piezoelectric Micropump Based on MEMS Flow Sensor," IEEE/RSJ International Conference on Intelligent Robots and Systems (IROS), Taipei, Oct. 18-20, 2010, pp. 3055-3060.
(Continued)

*Primary Examiner* — Roy Y. Yi
*Assistant Examiner* — Douglas Kay
(74) *Attorney, Agent, or Firm* — Christensen O'Connor Johnson Kindness PLLC

(57) ABSTRACT

A method for controlling pipetting operations done by a pipetting device having a system for measuring the flow rate of the liquid suctioned or dispensed and electronics to communicate with a computer. The method is based on detection of flow rate variations and the moments at which those variations occur. The method includes obtaining a curve of liquid flow rate by the pipette as a function of time, computing the first deviation of the curve, identifying and recording the maximum and minimum values of the first deviation and the moments at which the maximum and minimum values occur, comparing the maximum and mini-
(Continued)

mum values and the moments at which the maximum and minimum values occur with predetermined references for the values and the moments at which they occur, and based on the result of the comparison, providing a validation or error message.

23 Claims, 11 Drawing Sheets

(51) Int. Cl.
  *G01N 35/10* (2006.01)
  *G01F 25/00* (2006.01)
  *G01N 1/14* (2006.01)
  *G01F 11/02* (2006.01)

(52) U.S. Cl.
  CPC .. *G01N 35/1016* (2013.01); *B01L 2200/0684* (2013.01); *B01L 2200/143* (2013.01); *G01N 2035/1018* (2013.01)

(58) Field of Classification Search
  CPC .......... G01F 1/74; G01F 1/6965; B01L 3/021; B01L 2200/0684; B01L 2200/143; G01N 1/14; G01N 35/1016; G01N 2035/1018
  USPC ............................................................ 702/45
  See application file for complete search history.

(56) References Cited

U.S. PATENT DOCUMENTS

| | | | |
|---|---|---|---|
| 6,814,936 B1* | 11/2004 | Enhorning | B01L 3/0275 422/504 |
| 7,640,787 B2 | 1/2010 | Curtis | |
| 7,792,647 B1 | 9/2010 | Ding | |
| 7,917,313 B2 | 3/2011 | Ziegler | |
| 2002/0138213 A1* | 9/2002 | Mault | A61B 5/083 702/32 |
| 2004/0089051 A1 | 5/2004 | Camenisch | |
| 2006/0264766 A1* | 11/2006 | Bonan | A61B 5/0255 600/493 |
| 2013/0269800 A1* | 10/2013 | Fromont | G01M 13/00 137/565.16 |
| 2014/0010667 A1* | 1/2014 | Trump | F04B 49/002 417/20 |
| 2014/0073975 A1* | 3/2014 | Engelbrecht | A61B 5/7203 600/502 |
| 2015/0158177 A1* | 6/2015 | Fink | G01N 35/0099 700/245 |
| 2016/0313362 A1* | 10/2016 | Sugiyama | G01N 35/1016 |

OTHER PUBLICATIONS

Lee, D., et al., "Development of the Pipetting Error Sensor," Sensors and Actuators B: Chemical, 119(1):150-158, Nov. 2006.
International Search Report dated Jun. 18, 2014, issued in corresponding International Application No. PCT/EP2014/056551, filed Apr. 1, 2014, 4 pages.
Written Opinion of the International Searching Authority dated Jun. 18, 2014, issued in corresponding International Application No. PCT/EP2014/056551, filed Apr. 1, 2014, 6 pages.
International Preliminary Report on Patentability dated Dec. 29, 2015, issued in corresponding International Application No. PCT/EP2014/056551, filed Apr. 1, 2014, 1 page.

* cited by examiner

METHOD FOR CONTROLLING PIPETTING OPERATIONS

CROSS-REFERENCE TO RELATED APPLICATIONS

This application is a National Stage of International Application No. PCT/EP2014/056551, filed Apr. 1, 2014, which claims priority to European Application No. 13173422.0, filed Jun. 24, 2013.

TECHNICAL FIELD

The present invention relates to the field of pipetting and micro-pipetting operations. It more particularly relates to a control method making it possible to detect errors that may occur during operations performed using a pipetting device.

BACKGROUND OF THE INVENTION

Pipetting operations are often done in analysis procedures, during which liquid reagents must be assayed with great precision. Small quantities of liquid are suctioned from a reservoir and dispensed in a reactor, such as a well of a titration microplate. These pipetting operations are part of routine operations in many fields, in particular medical, chemical or pharmaceutical, and are often integrated into automatic procedures.

Naturally, it is very important to obtain a precise measurement of the volume of liquid suctioned and dispensed, but this is not sufficient. Indeed, it is still possible to encounter problems during a pipetting operation. For example, the reservoir may be empty or the end-piece of the pipette (also often called cone, point or tip) may not be entered into the liquid when the suction begins and, as a result, the pipette may suction air. The pipette may also leave the liquid before the end of the suction operation and suction air after having suctioned liquid. Furthermore, the end-piece of the pipette may also be blocked.

Consequently, in light of the high precision required in measuring the quantity of suctioned and dispensed liquid, in addition to the targeted applications, any problem occurring during a pipetting operation must be detected and reported so that no incorrect measurement may disrupt an analysis or assay.

U.S. Pat. No. 6,938,504 discloses a method for evaluating how an assay operation unfolds. It is proposed to obtain a curve that is characteristic, as a function of time, of at least one state variable of a substance present in the pipette. This characteristic curve is obtained for the entire duration of the assay operation. An analysis is next done to determine whether this characteristic curve is contained, for its entire duration, in an allowance range applied to a pre-established reference curve. Based on this analysis, a positive or negative result regarding the performance of the operation is then sent.

Such a method is interesting, but has several drawbacks. In particular, it is necessary to obtain and have in memory one or more reference curves (one for each external condition, such as the pipetted volume, the suction or dispensing speed, the type of liquid or the geometry of the tip). It is clear that the calibration of the system for detecting pipetting errors is very laborious.

Patent application WO 0188549 reveals a method for controlling the proper progression of a pipetting operation owing to the analysis of the atmospheric pressure measured in a suction tube of the device. A vacuum generator is connected by a suction tube to a pipette designed to suction and dispense liquid samples. According to the vacuum produced by the vacuum generator, the liquid is suctioned in the pipette or dispensed outside the pipette. An atmospheric pressure sensor is positioned on the suction tube connecting the vacuum generator and the pipette. Analyzing the pressure measured over a pipetting cycle makes it possible to verify the quality of the operation and detect operating anomalies.

This method has the drawback of only providing qualitative information on the pipetting operation. The measurement of the pressure of the air at the suction tube does not make it possible to determine the flow rate of the liquid flowing in the pipette or to calculate the volumes suctioned and dispensed during the pipetting operation.

The present invention aims to propose a method making it possible to avoid the aforementioned drawbacks.

BRIEF DESCRIPTION OF THE INVENTION

More particularly, the invention relates to a method for controlling pipetting operations done by a pipetting device comprising:
  a suction and dispensing tip designed to be submerged in a liquid reservoir to collect a certain quantity of that liquid,
  an inlet designed to be connected to a pressure or vacuum source,
  a system capable of measuring a value representing the flow rate of the liquid suctioned or dispensed during the pipetting operation,
  an electronic circuit controlling the pipetting operation and able to communicate information to a remote computer.

The method according to the invention is based on the detection of flow rate changes correlated to errors occurring during pipetting operations, during suction or dispensing, such as passages from air to liquid or from liquid to air, independently of the volumes and flow rates used. The method comprises the following steps:
  obtaining a curve representing the flow rate as a function of time of the liquid suctioned or dispensed by the pipette,
  calculating the first derivative of said curve,
  identifying and recording the maximum minimum vales of said first derivative and the moments at which the maximum and minimum values occur,
  comparing the maximum and minimum values and the moment at which the maximum and minimum values occur with predetermined references for said values and for the moment at which they occur,
  depending on the result of the comparison, providing a validation or error message.

BRIEF DESCRIPTION OF THE DRAWINGS

Other details and advantages of the invention will appear more clearly upon reading the following description, done in reference to the appended figures, in which.

DETAILED DESCRIPTION

Figure 1:
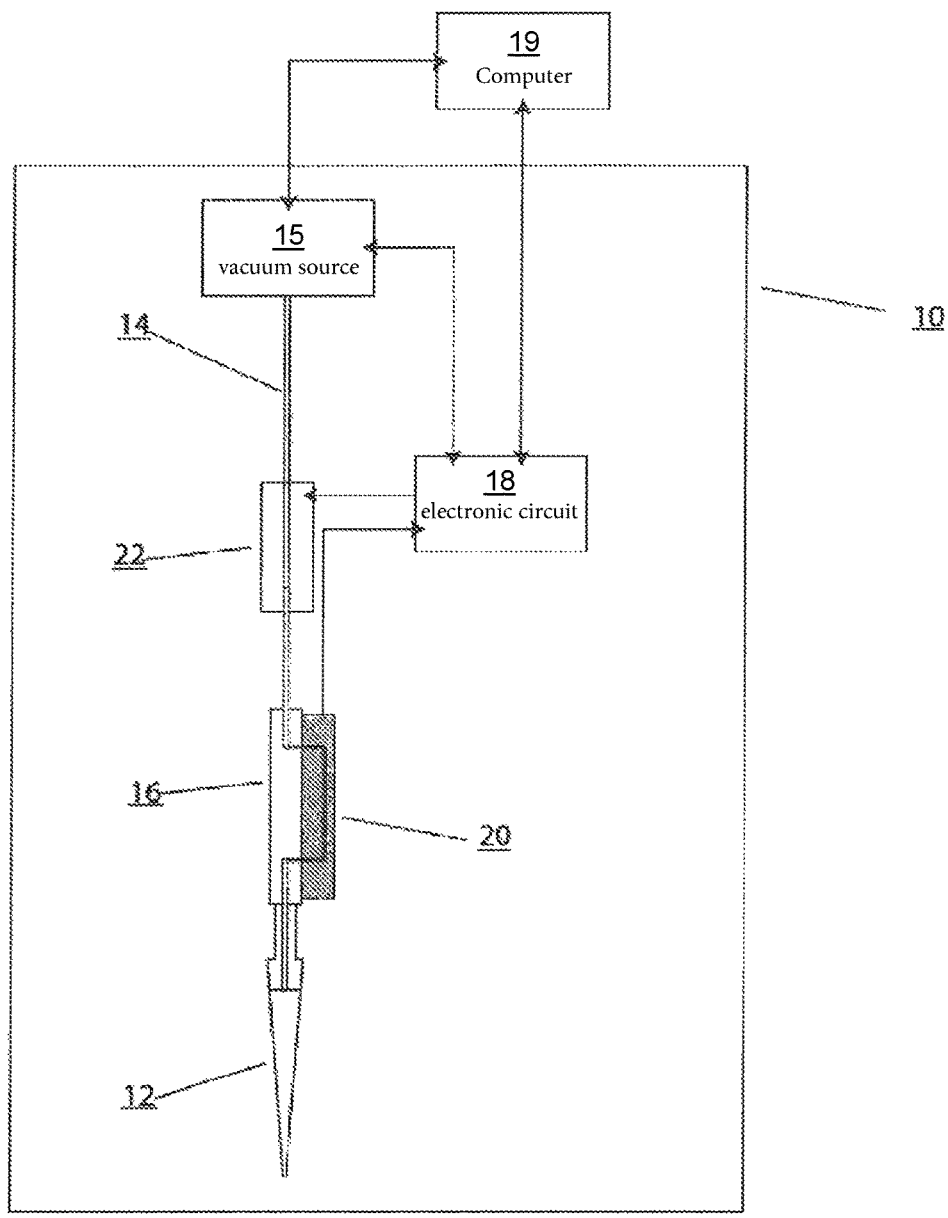
FIG. 1 is a schematic view of a pipetting device suitable for implementing the invention, FIGS. 2, 3, 4 and 5 propose curves obtained by the method according to the invention, for normal operation and for different abnormal suction situations, respectively, FIGS. 6 to 10 propose curves obtained using the method according to the invention, for normal operation and for different abnormal dispensing situations, respectively.

The method according to the invention is advantageously suitable for being used with a pipetting device 10, one example of which is illustrated in FIG. 1. Such a pipetting device 10 comprises a suction and dispensing tip 12 designed to be submerged in a liquid reservoir to collect a certain quantity of this liquid. The suction and dispensing tip can be a stationary cannula or a removable end-piece. The device 10 also comprises an inlet 14 designed to be connected to a pressure or vacuum source 15, a system 16 capable of measuring a value representing the flow rate of the liquid suctioned or dispensed during the pipetting operation and an electronic circuit 18 commanding the pipetting operation and able to communicate information to a remote computer 19.

The pipetting device can also comprise a valve 22, for example of the solenoid type, to open or close the connection between the inlet 14 and the system 16.

The pressure or vacuum system 15 may also be connected to a carrier fluid reservoir, not shown, the movements of this fluid driving the suction or dispensing of the liquid to be pipetted. Reference may be made to patent EP 1327152 incorporated by reference, in order to obtain a complete description of a pipetting device implementing a pipetting device with a carrier fluid. It will be noted that this carrier fluid can be liquid or gas.

Advantageously, the system 16 comprises a flow rate sensor 20, of the type measuring a pressure difference of the carrier fluid crossing through a fluid narrowing on the one hand and a temperature of the fluid through that narrowing on the other hand. Reference may be made to patent EP 1364188, incorporated by reference, to obtain a detailed description of this type of sensor.

In order to perform a pipetting operation, such as suction of the sample in the suction and dispensing tip 12, the remote computer 19 first adjusts the appropriate vacuum or overpressure level that the source 15 must apply and next sends the following sequence of instructions to the pipetting device (with one or more channels):
define the pipetting mode: suction or dispensing of the sample,
define the volume to be suctioned or dispensed as a function of the volume defined by the user,
send a command or activation signal to initiate the operation.

Once the command or activation signal has been received, the pipetting device first begins by calculating the setpoint for the volume to be collected, as a function of the received information. Calibration parameters of the sensor and other internal or external parameters can also be taken into account to calculate this setpoint. Next, the pipetting device begins the pipetting operation by opening the valve 22 and, at the same time, it begins the acquisition, continuously or at regular intervals, of the flow rate provided by the system 16 described above.

By integrating the acquired flow rate values in the time, the electronic circuit 18 determines the suctioned or dispensed volume. As long as the volume of liquid to be collected has not been reached, the pipetting device continues to acquire the flow rate, which is stored, at least sequentially, in a local memory, so as to be able to obtain a curve representative of the flow rate as a function of time, for the suctioned or dispensed liquid.

After the pipetting operation and according to the invention, the curve representing the flow rate as a function of time, recorded during the operation, is analyzed so as to detect a potential pipetting error.

The algorithm used to analyze the flow rate curve immediately after the pipetting operation includes the following steps. The first derivative of the flow rate curve is calculated. Then, on this first derivative, the maximum and minimum values are detected, as well as the moment at which these values have been reached over all of the data acquired during the measurement. Only these maximum and minimum values and the moment at which these values have been reached are stored in a memory of the electronic circuit 18. The derivative as such is not stored.

For a more effective determination of the errors, the maximum and minimum values of the first derivative of the flow rate curve are normalized, advantageously as a function of the flow rate, in order to make the error detection independent of this parameter.

By using the recorded information, i.e., the maximum and minimum values of the moment at which these values are reached, it is possible to diagnose a certain number of suction errors:
a tracking error if a suction operation begins in the liquid but ends in the air,
an air suction only, if the reservoir is empty,
a short sample if a suction operation begins in the air but ends in the liquid.

Figure 2:
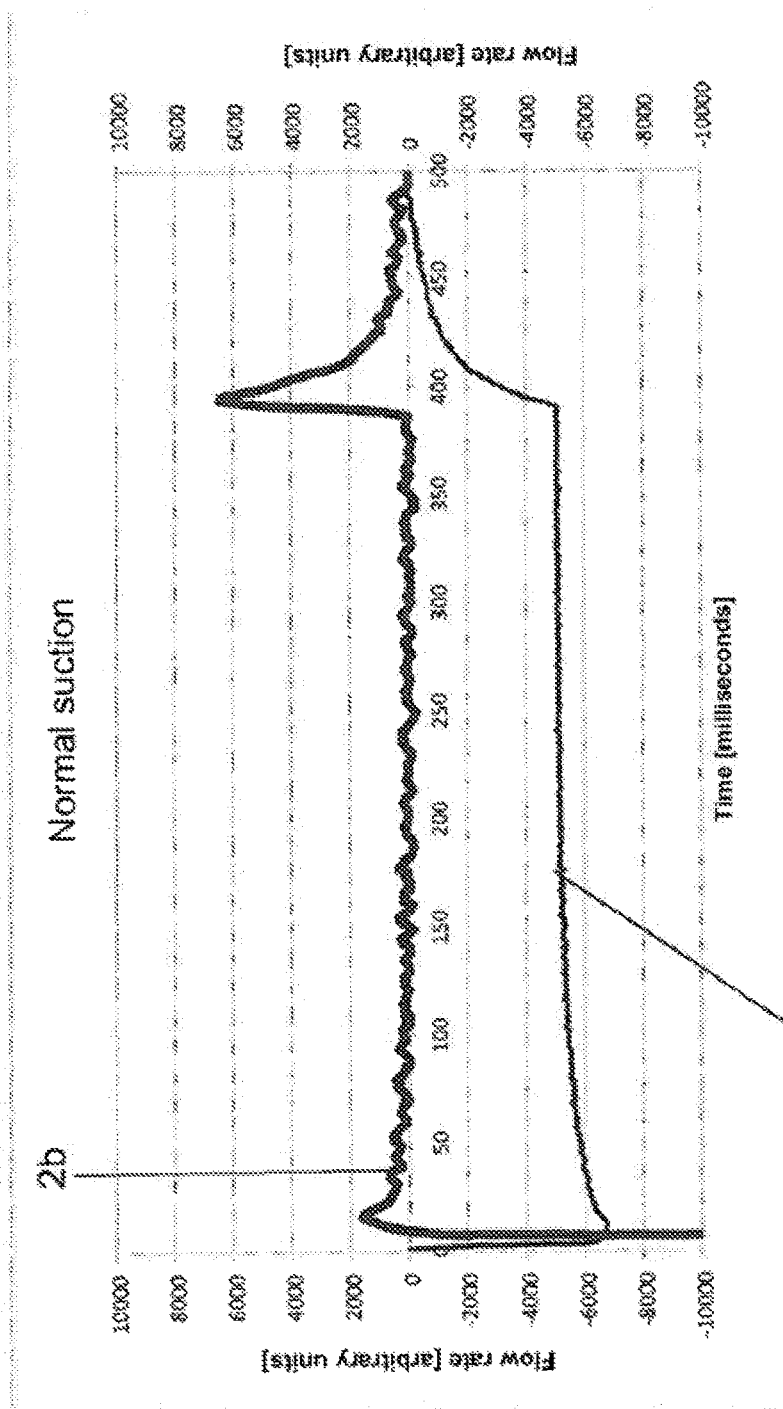

As a comparison, reference may be made to the curves shown in FIG. 2, which show a normal suction. Curve 2a shows the flow rate of the suctioned liquid, and curve 2b shows the first derivative of the flow rate according to an arbitrary unit. This curve 2b is analyzed, and one can see a minimum value at the beginning of the suction due to the opening of the valve. This first minimum is always present and has no impact or particular significance for the detection of an error. The algorithm will only begin the analysis after passing by this first minimum and, in the examples below, this initial minimum will be left out.

Subsequently, it is possible to observe a maximum value that occurs in an interval of 40 ms, preferably 30 ms after the beginning of the pipetting operation. This duration is typically the duration necessary to reach, under normal operating conditions of the pipetting device, a steady flow state of the liquid in the pipette. The notion of steady flow encompasses quasi-steady flow states.

It will be noted that, for normal suction, no minimum value is detected after the aforementioned initial minimum, with the understanding that a minimum value must be identified as being below a predetermined threshold. It will also be noted that, when the setpoint of the volume of liquid to be collected has been reached, the valve is closed and the flow rate returns to zero gradually.

Figure 3:
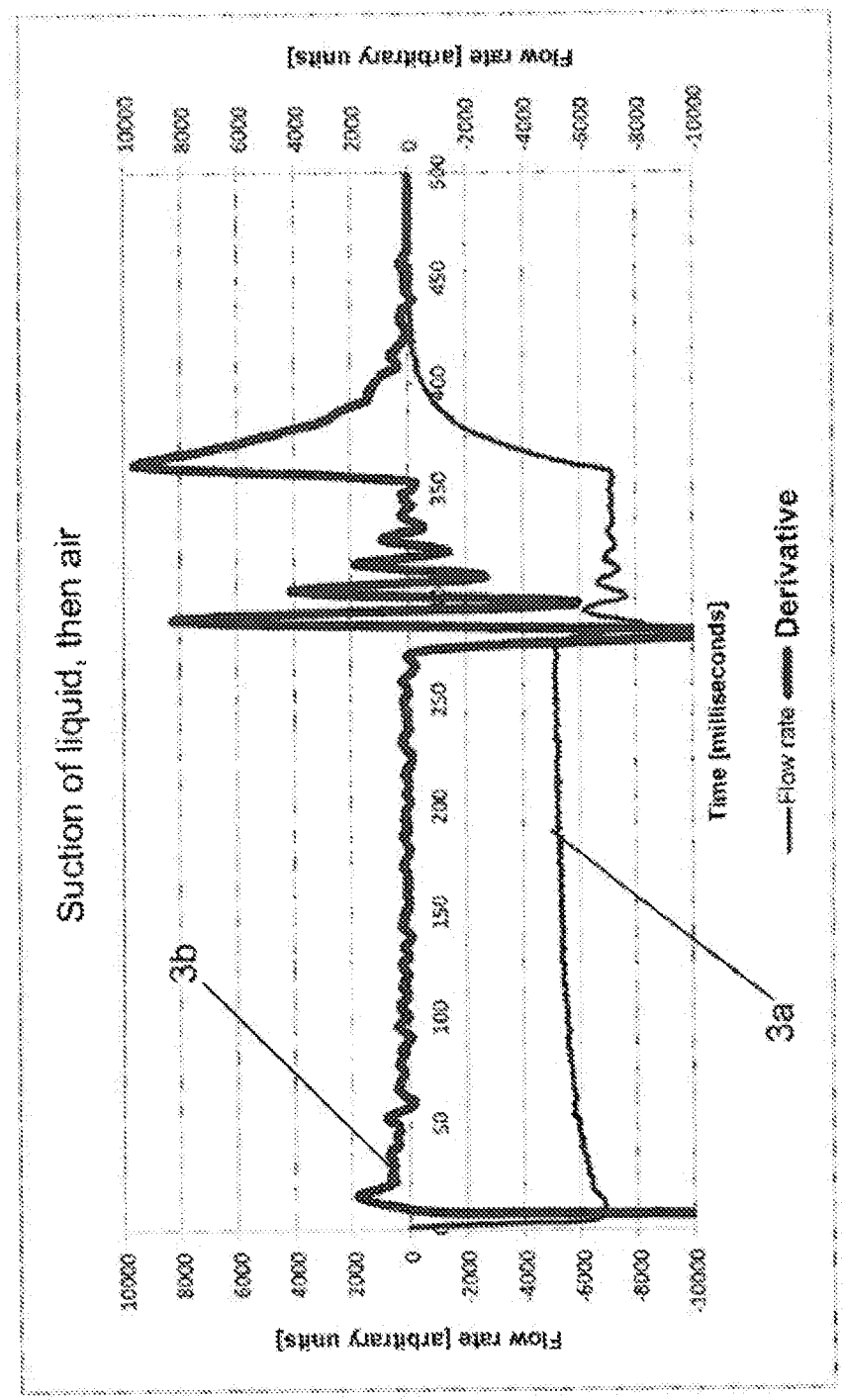

In FIG. 3, curve 3a shows the flow rate of the suctioned liquid and curve 3b shows the first derivative of the flow rate. Curve 3b is analyzed, and a minimum value, below the aforementioned predetermined threshold, is noted. During a suction operation, such a minimum value reveals a liquid-air passage of the dispensing and suction tip 12. If the presence of such a minimum value is detected during the operation, before the required volume has been suctioned, and if this minimum value is below said predetermined threshold, an error message is delivered indicating that, during the suction operation, the pipetting device has suctioned liquid, then air.

Figure 4:
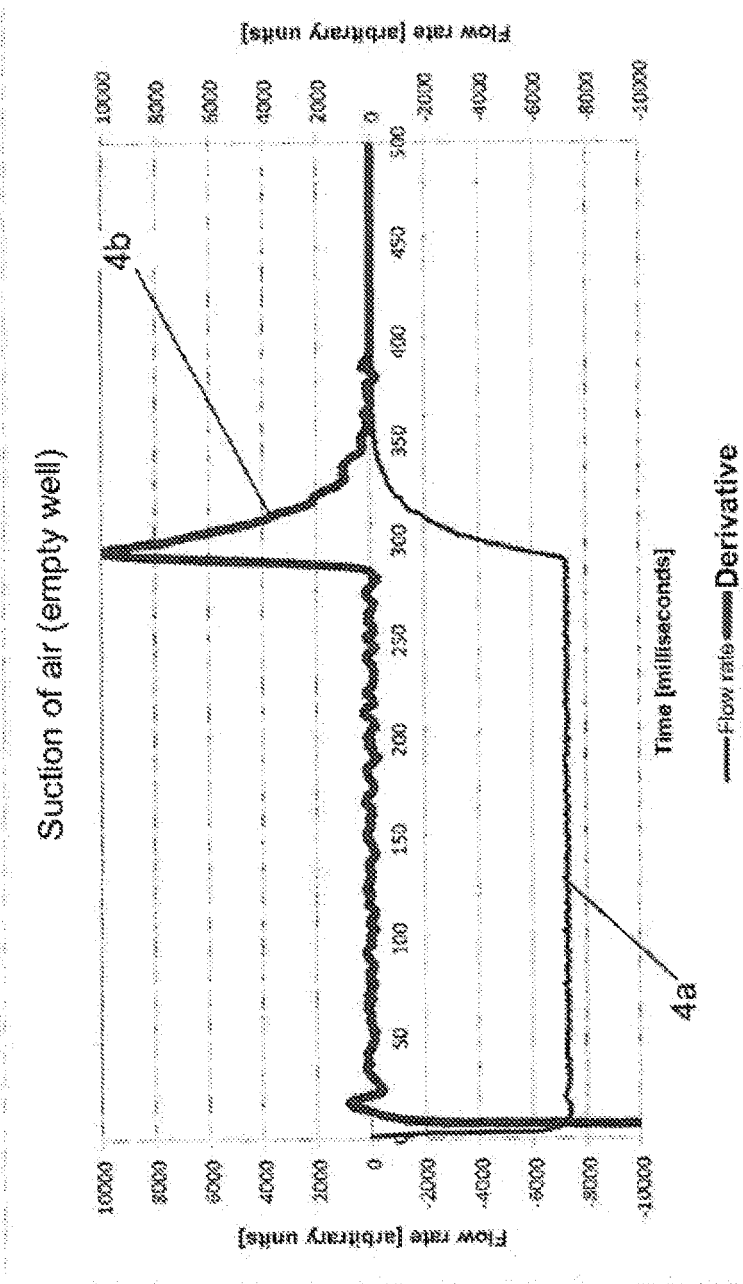

In FIG. 4, curve 4a shows the flow rate of the suctioned liquid and curve 4b shows the first derivative of the flow rate, and curve 4b is analyzed. Although a peak having a maximum value is detected around 30 ms after the beginning of the operation, this peak is smaller than what can be seen in FIG. 2. Thus, if the maximum value during the suction does not exceed the predetermined threshold, an error message is provided indicating that, during the pipetting operation, the device has suctioned air only. This means that the well in which the pipette performs its suctioning is empty or is at a lower level relative to the suction level of the pipette. If applicable, this analysis may be confirmed by detecting the absence of a minimum value below a predetermined threshold (typically, that of the analysis of FIG. 3). This absence means that there has not been any liquid-air transition, before suctioning air.

Figure 5:
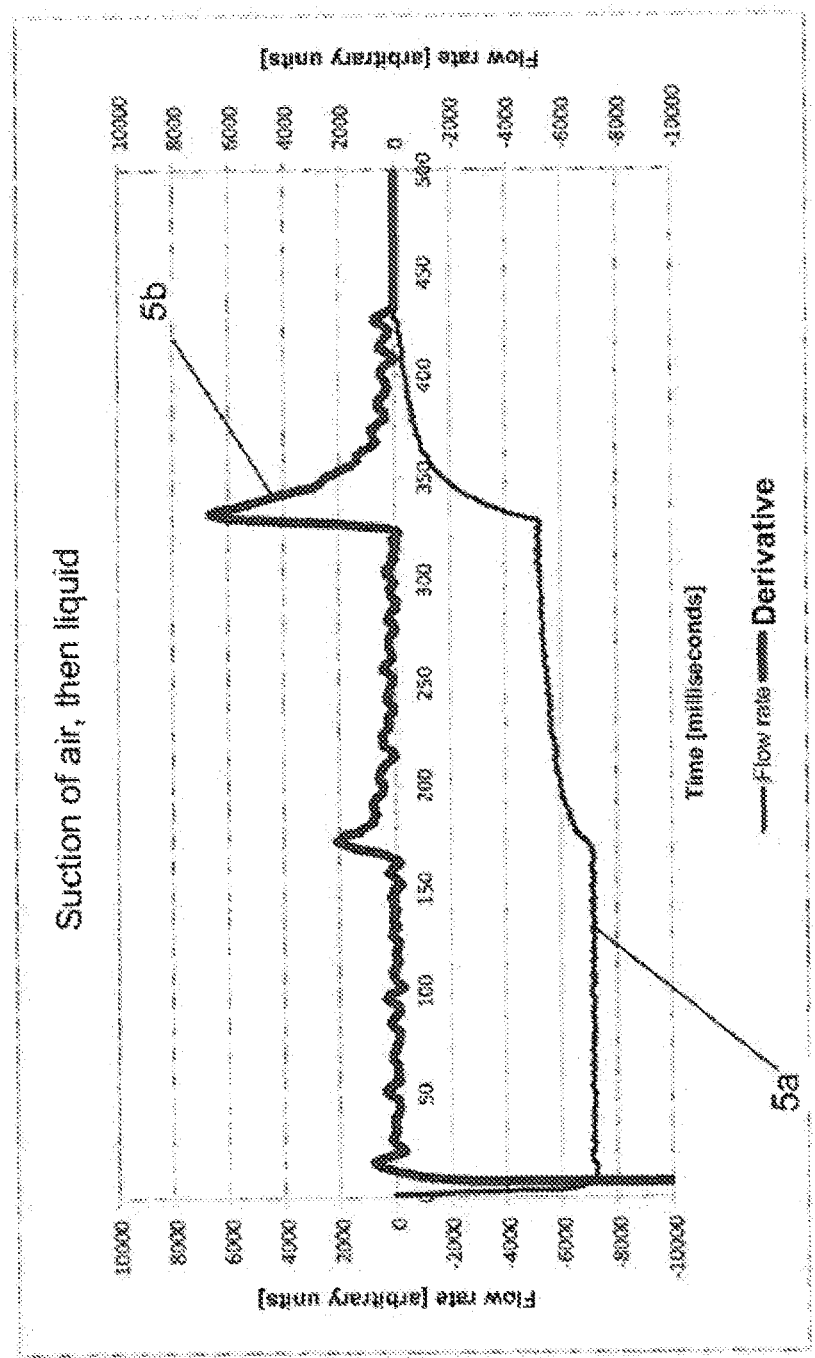

In FIG. 5, curve 5a shows the flow rate of the suctioned liquid and curve 5b shows the first derivative of the flow rate. Curve 5b is analyzed, and a peak is observed below the predetermined threshold from 30 ms after the beginning of the pipetting operation, as in FIG. 4. However, a more significant sized peak is observed around 180 ms after the beginning of the operation. This more significant sized peak can be compared with the maximum value of FIG. 2 and is considered to be above the predetermined threshold. In a suctioning operation, such a maximum value reveals an air-liquid passage of the suction and dispensing tip 12. However, if this maximum value occurs more than 40 ms, preferably more than 30 ms after the beginning of the pipetting operation, then an error message is emitted, signifying that the pipetting device has suctioned air before suctioning liquid.

It is also possible to combine several parameters so as to confirm an error message. For example, it is first possible to examine the minimum value of the first derivative and to verify whether this minimum value is below the predetermined threshold. As described above, this means that the device has suctioned liquid, then air. Then, the maximum value of the first derivative is considered, and it is verified whether this maximum value is above a predetermined threshold and whether this maximum value occurs within an interval of 40 ms, preferably 30 ms after the beginning of the pipetting operation, as in normal suctioning. This second step makes it possible to confirm that the pipetting device has suctioned liquid at the beginning of the operation.

It is also first possible to consider the maximum value of the first derivative. If the maximum value is above a predetermined threshold and if this maximum value occurs after the necessary time, under normal operating conditions of the pipetting device, to reach a steady flow state of the liquid in the pipette, preferably after 30 ms, preferably after 40 ms after the beginning of the pipetting operation, this means, as described above, that the device has suctioned air, then liquid. Then, still considering the maximum value of the first derivative, as in the case of air suction only, the absence of a maximum above the predetermined threshold before the time needed, under normal operating conditions of the pipetting device, to reach a steady flow state of the liquid in the pipette is detected, making it possible to confirm that the pipetting device has suctioned air at the beginning of the operation.

By analogy with the suction errors described above, it is possible to use the same information, i.e., the maximum and minimum values and the moment at which these values are reached, to detect anomalies during the dispensing operation:

dispensing air only, if the end-piece is empty;
a short sample (over-dispensing) if a dispensing operation begins with liquid, but ends with air;
dispensing of air before distributing liquid (trailing air gap);
dispensing air before and after distributing liquid (trailing air gap and over-dispensing).

It should be noted that the sign of the flow rate for dispensing is the inverse of that for suctioning. Consequently, for comparable situations, a minimum then becomes a maximum and vice versa.

Figure 6:
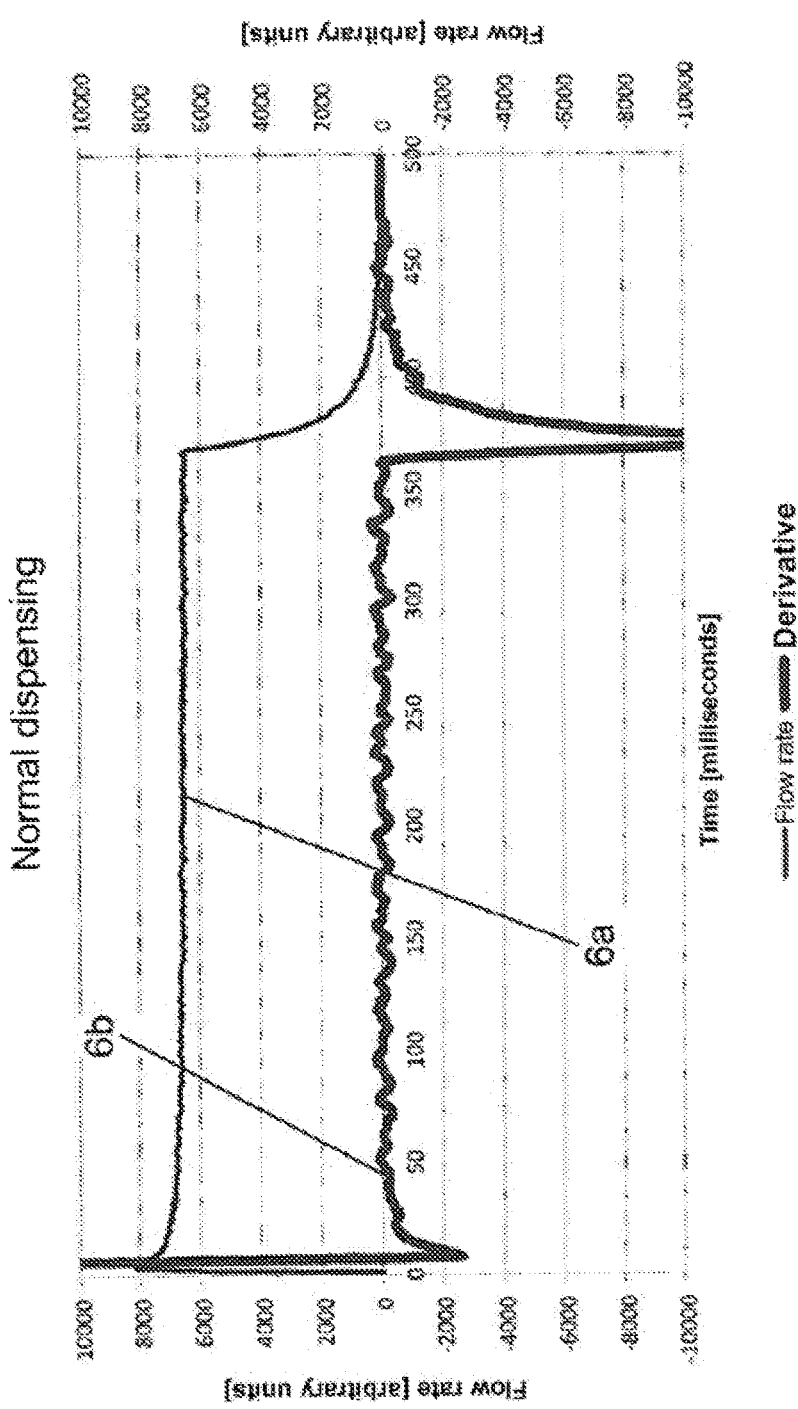

As a comparison, FIG. 6 proposes curves obtained for a normal dispensing operation. Curve 6a shows the flow rate of the suctioned liquid and curve 6b shows the first derivative of the flow rate. Curve 6b is analyzed, and one can see a maximum value at the beginning of dispensing due to the opening of the valve. This first maximum is still present and has no impact or particular meaning for the detection of an error. The algorithm only begins the analysis after passing by this first maximum and, in the examples below, this initial maximum will be set aside. It is also possible to note the presence of a minimum value exceeding the predetermined threshold, during the necessary time, under normal operating conditions of the pipetting device, to reach a steady flow state of the liquid in the pipette. This duration is typically approximately 40 ms, more specifically less than 30 ms. A regular flow rate curve is next also observed, without a real minimum or maximum value relative to predetermined threshold, during the progression of the operation and until triggering the end of dispensing, when the flow rate begins to drop.

Figure 7:
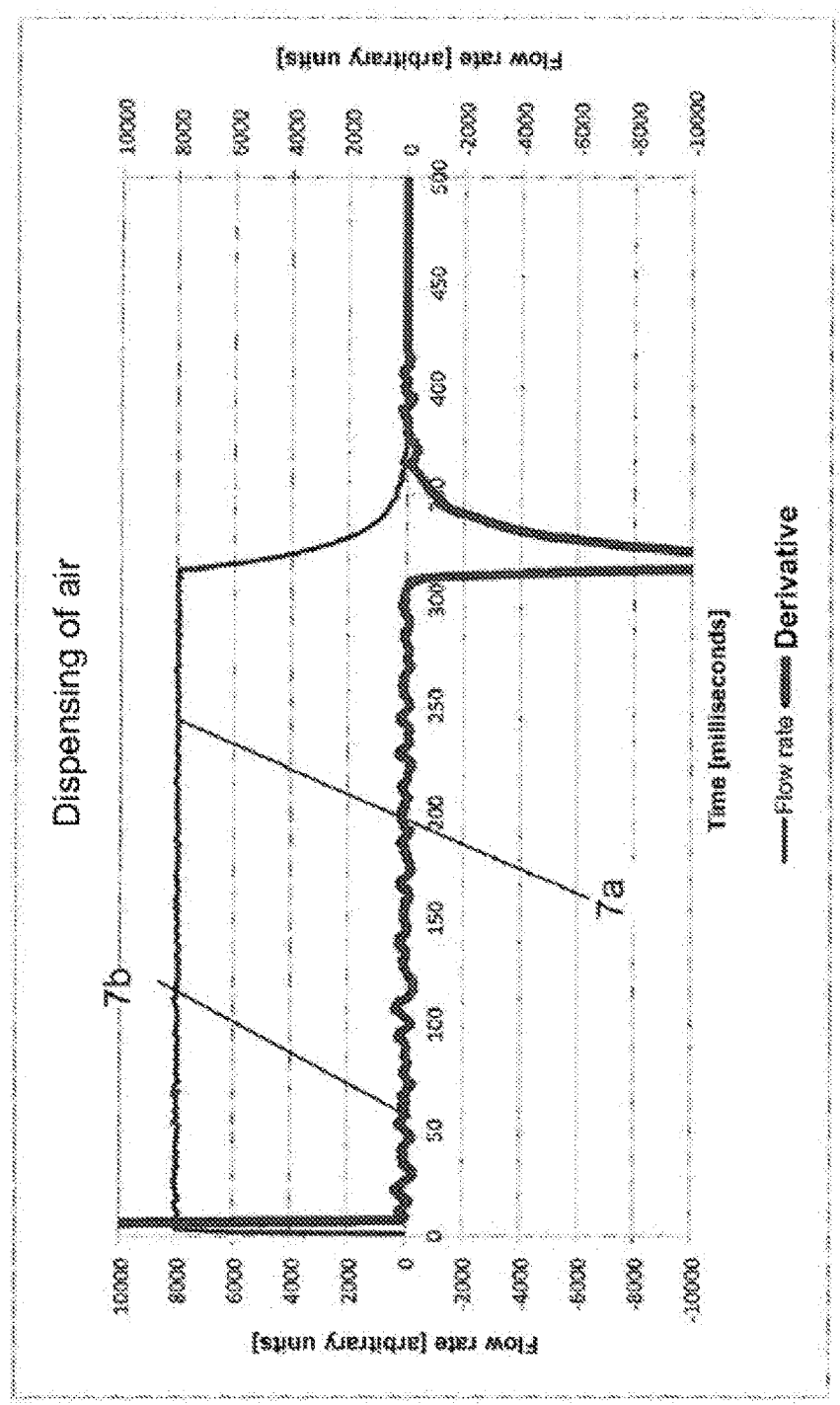

In FIG. 7, curve 7a shows the flow rate of the dispensed liquid and curve 7b shows the first derivative of the flow rate. Curve 7b is analyzed, and the presence or absence of a minimum value, below a predetermined threshold, is detected. The absence of such a minimum value during the dispensing operation results in an error message indicating the dispensing of air only. This detection can be confirmed by the absence of a maximum above a predetermined threshold during dispensing.

Figure 8:
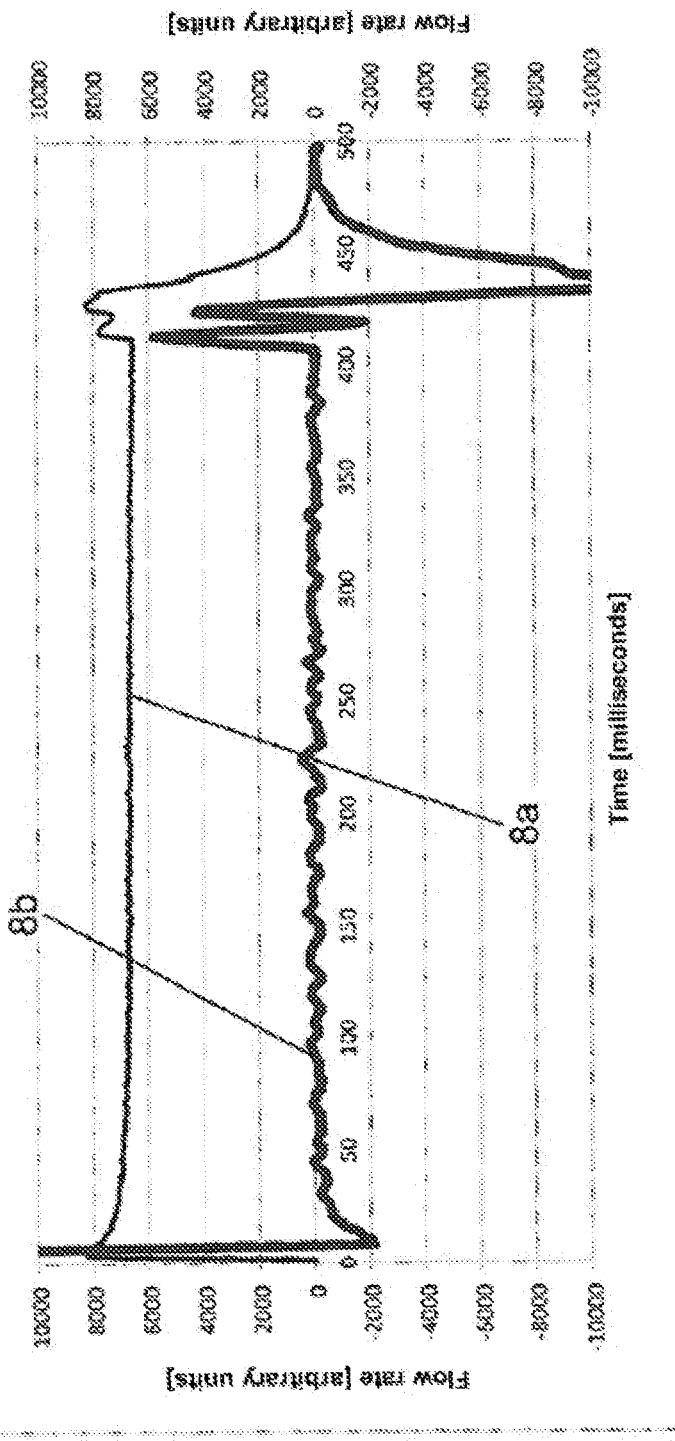

In FIG. 8, curve 8a shows the flow rate of the dispensed liquid and curve 8b shows the first derivative of the flow rate. Curve 8b is analyzed, and the presence of a maximum value is detected, above a predetermined threshold. In a dispensing operation, such a maximum value reveals a liquid-air passage in the suction and dispensing tip 12. This maximum is situated after a time interval of 40 ms, preferably 30 ms, necessary to establish a steady flow state of the liquid in the pipette. The presence of such a maximum value results in an error message indicating the dispensing of air after dispensing a liquid sample (over-dispensing phenomenon).

Figure 9:
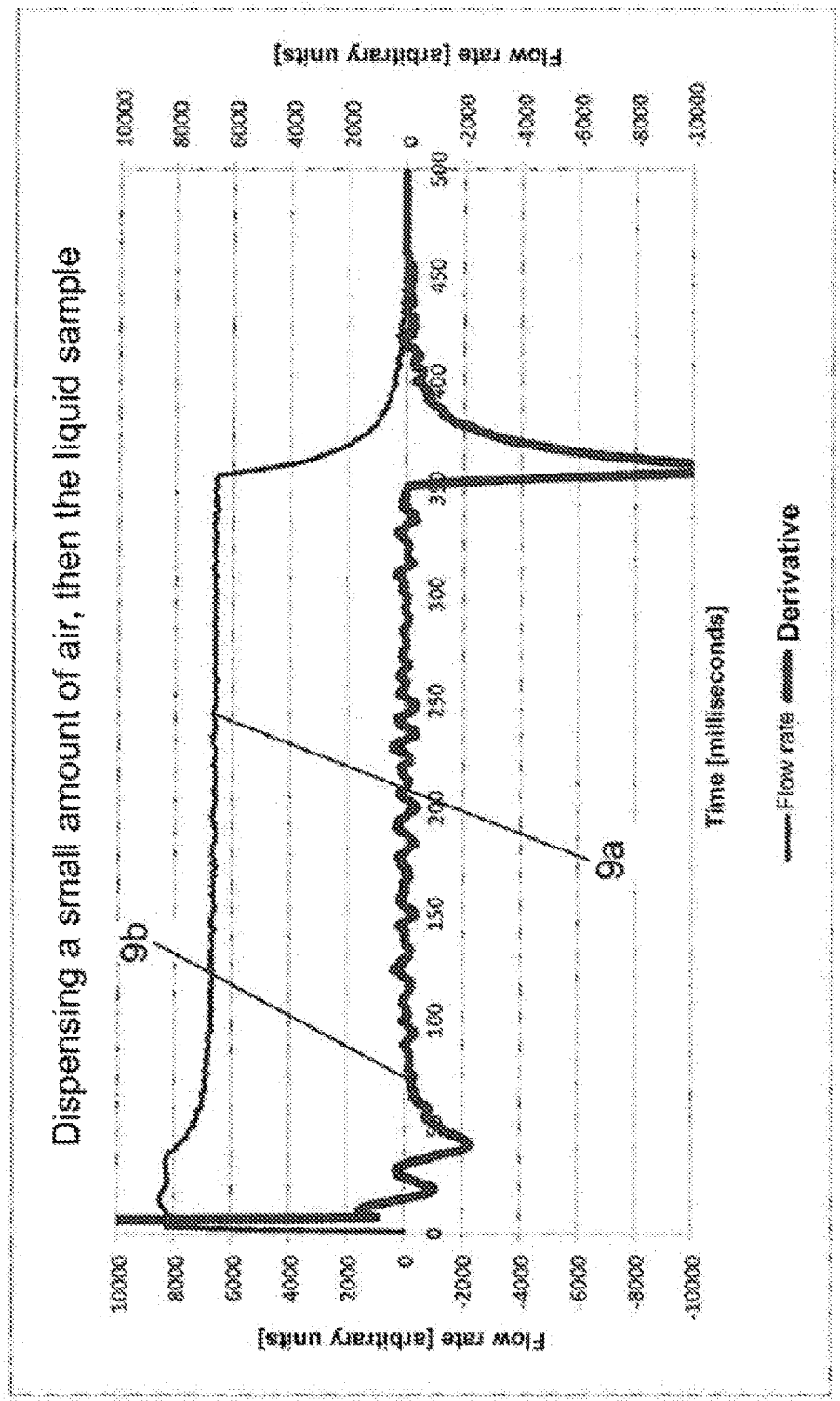

In FIG. 9, curve 9a shows the flow rate of the dispensed liquid and curve 9b shows the first derivative of the flow rate. Curve 9b is analyzed and the presence of a minimum value is detected, below a predetermined threshold. In a dispensing operation, such a minimum value reveals an air-liquid passage of the suction and dispensing tip 12. If this minimum value is situated after a time interval necessary to establish a steady flow state of the liquid in the pipette, preferably after 30 ms, preferably after 40 ms, the presence of such a minimum value results in an error message indicating dispensing of air before dispensing of the liquid sample.

It is also possible to combine several parameters so as to confirm an error message. For example, it is first possible to examine the maximum value of the first derivative. If a maximum value is observed above a predetermined threshold, this means, as described above, that the device has dispensed liquid, then air. Then, the minimum value of the first derivative is considered. The presence of a minimum below the predetermined threshold before the time needed, under normal operating conditions of the pipetting device, to reach a steady flow state of the liquid in the pipette, similar to normal dispensing, makes it possible to confirm that the pipetting device has dispensed liquid at the beginning of the operation.

It is also first possible to consider the minimum value of the first derivative. If a minimum value is detected below the predetermined threshold, after the time needed, under normal operating conditions of the pipetting device, to reach a steady flow state of the liquid, then as described above, this means that the device has dispensed air, then liquid. Then, as in the case of dispensing air only, the minimum value of the first derivative is considered, for liquid only, and the absence of such a minimum value below a predetermined threshold is verified, before the time needed, under the normal operating conditions of the pipetting device, to reach a steady flow state of the liquid, preferably in an interval of 40 ms, preferably of 30 ms after the beginning of the pipetting operation. This second step makes it possible to confirm that the pipetting device has dispensed air at the beginning of the operation.

Figure 10:
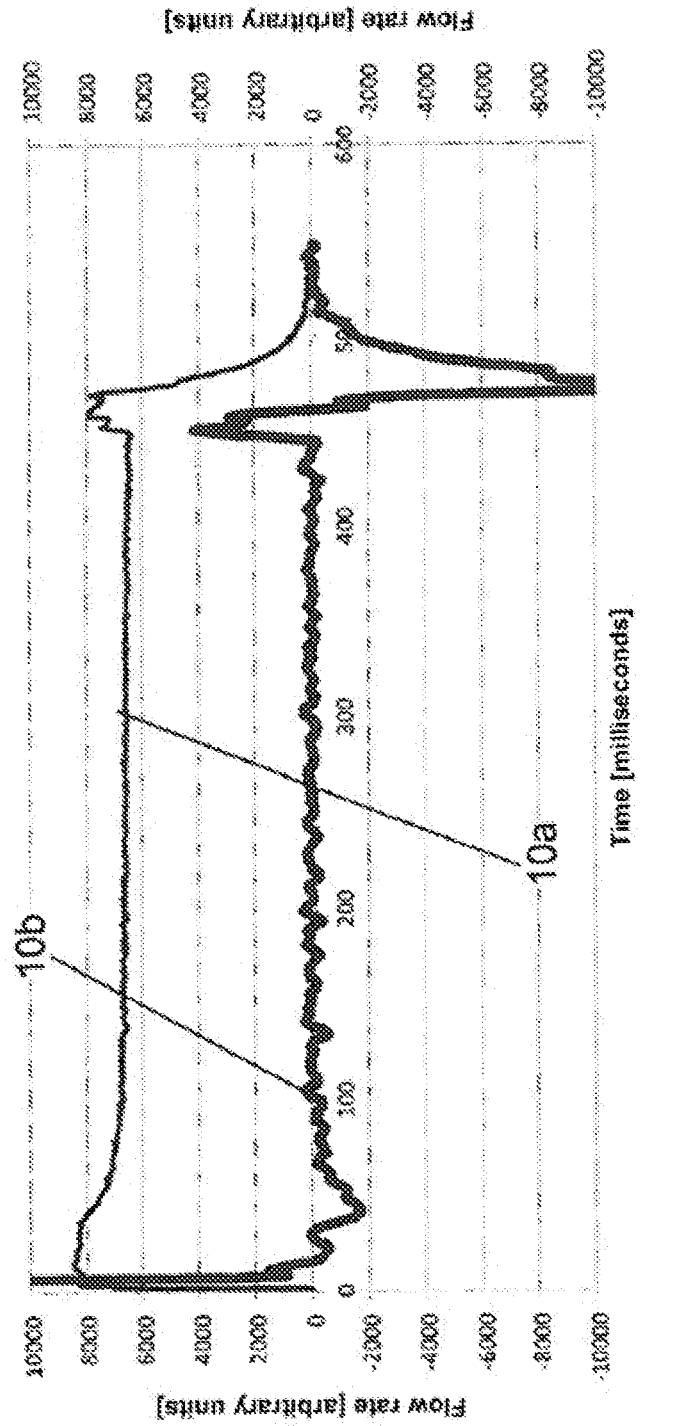

In FIG. 10, curve 10a shows the flow rate of the dispensed liquid and curve 10b shows the first derivative of the flow rate. The illustrated situation is the combination of FIGS. 8 and 9. Both a minimum value beyond the time interval of 40 ms and a maximum value that comes after the minimum are detected. An error message meaning that air has been dispensed at the beginning and end of the operation, with liquid dispensing between the two air dispensing operations, is then sent.

The method according to the invention therefore makes it possible to detect erroneous events that may occur during pipetting operations, during suction or dispensing, independently of the volumes and flow rates used.

In addition to the error detection done after a pipetting operation, the method according to the invention proposes combining a real-time error detection, which makes it possible to obtain good precision and very good relevance in the error detection.

Figure 11:
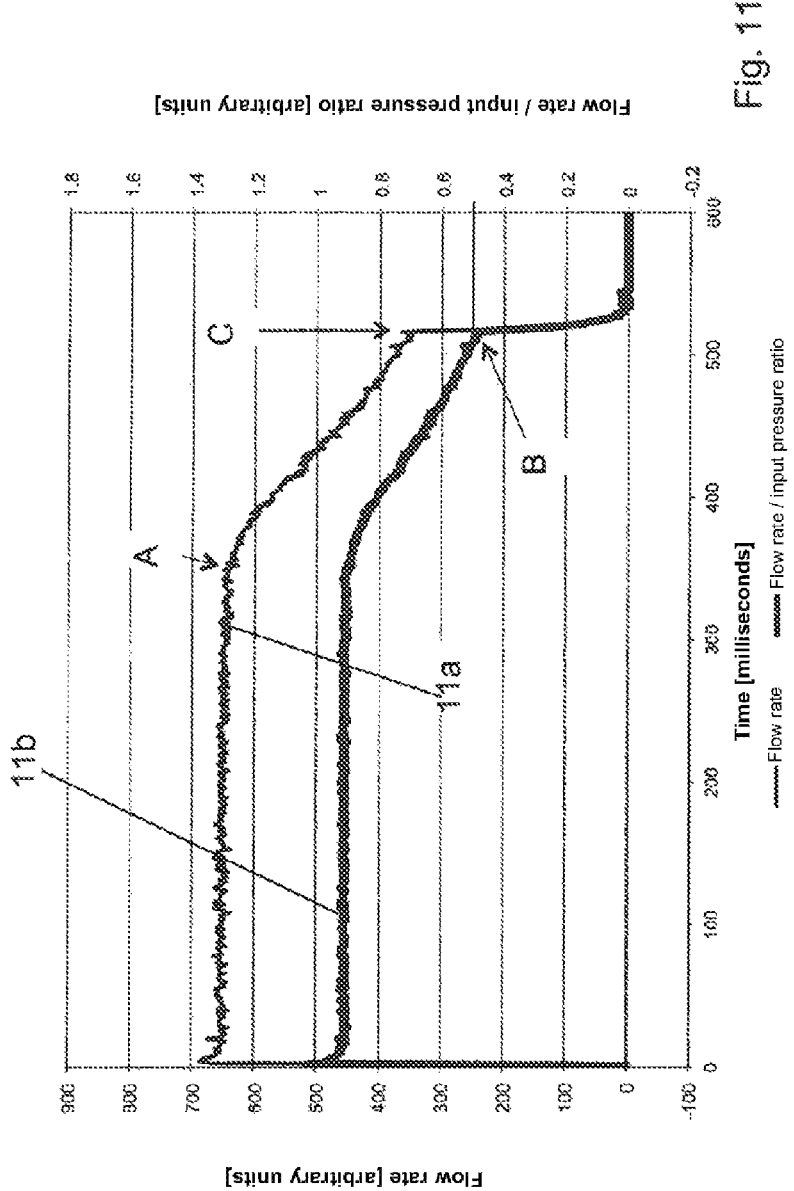
FIG. 11 shows curves obtained upon detection of an occlusion.

To that end, during the operation, the sign of the acquired flow rate is compared with predefined thresholds in order to ensure that the adjustment of the vacuum or pressure in the pipetting device indeed complies with the stipulated operation (suction or dispensing). At the same time, it is verified whether the suction and dispensing tip is plugged or obstructed by calculating the ratio of the measured flow rate to the adjustment value of the pressure and comparing this ratio to a predetermined threshold. For example, in FIG. 11, the flow rate is shown on curve 11a and the flow rate/input pressure ratio on curve 11b. The occlusion begins at arrow A and the flow rate drops gradually. An error message is sent when the ratio reaches, for example, the threshold of 0.5 (arrow B). The operation is then stopped (arrow C) and it is observed that the flow rate drops to 0.

Furthermore, the time elapsed since the beginning of the operation is compared with a predefined maximum duration. If the elapsed time is shorter than the predefined maximum duration, the operation continues. Otherwise, the operation is stopped.

The real-time control also makes it possible to stop the pipetting operation if there is not enough liquid and if air is suctioned or dispensed. To that end, the calculation of the derivative at an interval reduced by several milliseconds makes it possible to command the pressure or vacuum source 15 or the valve 22 if a pre-established limit value is exceeded. In the case of FIG. 3, the strong decrease in the value of the derivative around 300 ms corresponds to air suctioning. The comparison, after the beginning of suctioning, of the value of the flow rate derivative with predefined value causes the suctioning to stop if the value of the derivative is below this value. In the example of FIG. 8, the strong increase of the value of the derivative around 400 ms corresponds to air dispensing. Comparing, after the beginning of the dispensing, the value of the flow rate derivative with a predefined value causes the dispensing to stop if the value of the derivative is above this value.

When the suction and dispensing tip implements an end-piece, the latter as such is not part of the pipetting device. However, the dimensions of the end-piece can influence, ideally improve, the error detection method carried out after a pipetting operation, as described above. A smaller diameter of the end-piece will improve the "resolution" of the method by improving the intensity of the minimum and maximum values. One skilled in the art will be capable, from tests and routine experiments, of optimizing the ratio between the diameter of the end-piece and the diameter of the fluid narrowing of the sensor, so as to improve the resolution of the first derivative of the curve of the flow rate as a function of time. The optimization of the dimensions of the end-piece can be considered a preliminary step of the error detection method according to the invention. The numerical values of the detection thresholds for the minimum and maximum of the derivative can be chosen as a function of the end-piece used.

It has been seen above how studying and comparing the maximum and minimum values of the derivative of the flow rate and the moments at which they occur makes it possible to identify the beginning and end of a pipetting operation. For a suction operation, the passage from air to liquid is detected and associated with the beginning of suctioning. The passage from liquid to air is detected and associated with the end of suctioning. For a dispensing operation, it has been described above, in connection with FIG. 6, that it is possible to identify the beginning and end of dispensing.

Knowing this data makes it possible to obtain the suctioned or dispensed volume of liquid. To that end, it is appropriate to calculate the integral of the curve showing the flow rate as a function of time between the beginning and end of a suction or dispensing phase of the liquid. The obtained value represents the volume of the suctioned or dispensed liquid.

The invention claimed is:

1. A method for validating pipetting operations carried out with a pipetting device, said pipetting device comprising:
   a suction and dispensing tip designed to be submerged in a liquid reservoir to collect a certain quantity of that liquid, an inlet designed to be connected to a pressure or vacuum source,
   an electronic circuit controlling the pipetting operation, and a system capable of measuring a value representing the flow rate of the liquid suctioned or dispensed during the pipetting operation,
   wherein the method is based on the detection of flow rate variations and the moment at which these variations occur during pipetting operations, and comprises the following steps of:
   acquiring flow rate values in time during pipetting operations by means of a flow rate sensor in the system and connected to the electronic circuit;
   storing said flow rate values in a memory;
   obtaining, after pipetting operations, from said flow rate values stored in said memory a curve representing the flow rate as a function of time of the liquid suctioned or dispensed by the pipette;

calculating the first derivative of said curve;

identifying the maximum and minimum values of said first derivative and the moments at which the maximum and minimum values occur;

detecting a pipetting error relating to dispensing or suctioning air or liquid by comparing the maximum and minimum values of the first derivative and the moment at which the maximum and minimum values occur with predetermined references for said values and for the moment at which they occur;

and providing an error message and stopping the pipetting device to prevent a pipetting operation problem based on the comparison.

2. The method according to claim 1, comprising providing an error message indicating that the pipetting device has suctioned liquid then air if the minimum value of said first derivative is below a first predetermined threshold before the end of said suction.

3. The method according to claim 1, comprising providing an error message indicating that the pipetting device has suctioned air only if the maximum value of the first derivative is below a second predetermined threshold.

4. The method according to claim 3, comprising providing an error message indicating that the device has suctioned only air if no value below the first predetermined threshold is detected on said derivative and no value above the second predetermined threshold is detected.

5. The method according to claim 1, comprising providing an error message indicating that the pipetting device has suctioned air then liquid if the maximum value of the first derivative is above a second predetermined threshold and said maximum value occurs later than 30 ms after the beginning of the pipetting operation.

6. The method according to claim 2, wherein the minimum value of the first derivative is first considered according to the method of claim 2, then considering the maximum value of the first derivative if said minimum value of the first derivative occurs before the quantity of liquid to be collected is suctioned and said minimum value of the first derivative is below the first predetermined threshold, wherein the presence of a maximum value of the first derivative above the second predetermined threshold before 30 ms after the beginning of the pipetting operation verifies that the pipetting device has suctioned liquid at the beginning of the operation then air.

7. The method according to claim 5, wherein the maximum value of the first derivative is first considered according to claim 5, then considering the maximum value of the first derivative if the maximum value of the first derivative is above the second predetermined threshold and said maximum value of the first derivative occurs later than 30 ms after the beginning of the pipetting operation, wherein the absence of the maximum value of the first derivative above the second predetermined threshold before the 30 ms verifies that the pipetting device has suctioned air at the beginning of the operation then liquid.

8. The method according to claim 1, comprising providing an error message indicating that the device has dispensed air after having dispensed the sample if a maximum value of the first derivative is detected above a first predetermined threshold.

9. The method according to claim 1, comprising providing an error message indicating that the device has dispensed only air if the minimum value of the first derivative detected during a dispensing operation is above a second predetermined threshold.

10. The method according to claim 9, comprising detecting the absence of a maximum value of the first derivative above a first predetermined threshold during the dispensing operation, and providing the error message indicating that the device has dispensed only air if, during a dispensing operation, there is no detection of a minimum value of the first derivative below the second predetermined threshold and no maximum value of the first derivative above the first predetermined threshold.

11. The method according to claim 1, comprising providing an error message indicating that the device has dispensed air before having dispensed the sample if a minimum value of the first derivative is detected below the second predetermined threshold later than 30 ms after the beginning of the pipetting operation.

12. The method according to claim 8, wherein the maximum value of the first derivative is first considered according to the method of claim 8, then the minimum value of the first derivative is considered if said maximum value of the first derivative occurs before the quantity of liquid to be collected is dispensed and said maximum value of the first derivative is above the first predetermined threshold, wherein the presence of a minimum value below the second predetermined threshold before the time needed, under the normal operating conditions of the pipetting device, to achieve a steady flow state of the liquid in the pipette making it possible to verify that the pipetting device has dispensed liquid at the beginning of the operation, then air.

13. The method according to claim 11, wherein the minimum value of the first derivative is first considered according to claim 11, then said minimum value of the first derivative is considered if the minimum value of the first derivative is below the second predetermined threshold and said minimum value occurs later than 30 ms after the beginning of the pipetting operation, wherein the absence of a minimum value below the second predetermined threshold before 30 ms verifies that the pipetting device has dispensed air at the beginning of the operation then liquid.

14. The method according to claim 11, comprising providing an error message indicating that the device has dispensed air, then liquid, then air if more than 30 ms after the beginning of the pipetting operation, there is a detection of both a minimum value of the first derivative below the second predetermined threshold and a maximum value of the first derivative above the first predetermined threshold, wherein said maximum value of the first derivative is detected at a moment after the detection time of the minimum value of the first derivative.

15. The method according to claim 1, wherein the maximum and minimum values of the first derivative of said curve are normalized as a function of the flow rate and in that actions taken on exceeding the predetermined thresholds are related to the normalized values.

16. The method according to claim 1, wherein a real-time error detection is implemented during the step for obtaining the curve representative of the flow rate.

17. The method according to claim 16, wherein said real-time error detection involves a step to verify the direction of the measured flow to confirm that an appropriate pressure or vacuum is applied for a dispensing or suction operation, respectively, and the operation is continued if the direction of the measured flow corresponds to the dispensing or suction operation requested by a user, otherwise, the operation is stopped.

18. The method according to claim 16, wherein said real-time error detection involves a step for calculating a ratio of the measured flow rate divided by a pressure adjustment value, and comparing said ratio with a predetermined threshold, and the operation is continued if said ratio is above said predetermined threshold, otherwise, the operation is stopped.

19. The method according to claim 16, wherein said real-time error detection involves a step for comparing the time elapsed since the beginning of the operation with a predefined maximum duration, and the operation continues if the elapsed time is shorter than the predefined maximum duration, otherwise, the operation is stopped.

20. The method according to claim 16, wherein said real-time error detection includes a step for comparing, from the beginning of the suction, the value of the derivative of the flow rate with a predefined value, and if the value of the derivative is below the predefined value, the suction operation is stopped.

21. The method according to claim 16, wherein said real-time error detection includes a step for comparing, from the beginning of the dispensing, the value of the derivative of the flow rate with a predefined value, and if the value of the derivative is above the predefined value, the dispensing operation is stopped.

22. The method according to claim 1, wherein said system capable of measuring a value representing the flow rate of the suctioned or dispensed liquid is provided with a flow rate sensor and wherein the suction and dispensing tip is provided with a removable end-piece positioned to penetrate in the liquid to be suctioned, wherein the ratio of the diameter of the end-piece to the diameter of the sensor is optimized to improve the resolution of the first derivative of the curve representing the flow rate as a function of time.

23. The method according to claim 1, comprising a step for calculating the volume of the suctioned or dispensed liquid, said volume calculation being obtained by:
  identifying, from the maximum and minimum values of the first derivative, the beginning and end of a suction or dispensing operation, and
  integrating the flow rate as a function of time between the values previously determined of the beginning and end of the suction or dispensing operation.

* * * * *